(12) United States Patent
Buettner et al.

(10) Patent No.: US 8,197,136 B2
(45) Date of Patent: Jun. 12, 2012

(54) TOMOGRAPHY APPARATUS WITH AN ANNULAR AIRFLOW CHANNEL WITH AN AIR-DIVERTING VENTILATION ELEMENT

(75) Inventors: Thorsten Buettner, Pretzfeld (DE); Rita Krug, Fuerth (DE); Andreas Speck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 175 days.

(21) Appl. No.: 12/820,366

(22) Filed: Jun. 22, 2010

(65) Prior Publication Data
US 2010/0322374 A1  Dec. 23, 2010

(30) Foreign Application Priority Data
Jun. 23, 2009  (DE) .......................... 10 2009 030 008

(51) Int. Cl.
*H05G 1/02* (2006.01)
*H01J 35/02* (2006.01)
(52) U.S. Cl. ........................................ 378/199; 378/193
(58) Field of Classification Search ................ 378/4–20, 378/141, 193, 199, 204, 210
See application file for complete search history.

(56) References Cited

U.S. PATENT DOCUMENTS

| | | | |
|---|---|---|---|
| 7,488,949 B2 * | 2/2009 | Ueno et al. | 250/370.15 |
| 2004/0202287 A1 | 10/2004 | Muller | |
| 2004/0228450 A1 | 11/2004 | Mueller | |
| 2007/0053500 A1 | 3/2007 | Distler et al. | |
| 2007/0284535 A1 * | 12/2007 | Heismann et al. | 250/370.15 |
| 2009/0041181 A1 * | 2/2009 | Krug | 378/19 |
| 2009/0279660 A1 * | 11/2009 | Takamatsu et al. | 378/19 |

FOREIGN PATENT DOCUMENTS
DE  20 2004 015 522 U1  1/2005

* cited by examiner

*Primary Examiner* — Anastasia Midkiff
(74) *Attorney, Agent, or Firm* — Schiff Hardiff LLP

(57) ABSTRACT

A tomography apparatus has an annular channel and at least one ventilation element for the purpose of drawing off an air current flowing through the annular channel. The ventilation element contains an intake window that is located in the annular channel for the purpose of drawing off at least a portion of the air current. In order to obtain an even flow profile at an output window of the ventilation element, the intake window has a greater effective intake cross-section at both sides than at the middle. By such evening the flow profile at the output window, turbulence and air current interruptions of the air can be generally avoided, such that when operating the tomography apparatus, disrupting acoustic emissions may be reduced, or a higher air flow and thereby a greater cooling effect may be obtained.

8 Claims, 4 Drawing Sheets

TOMOGRAPHY APPARATUS WITH AN ANNULAR AIRFLOW CHANNEL WITH AN AIR-DIVERTING VENTILATION ELEMENT

BACKGROUND OF THE INVENTION

1. Field of the Invention

The invention concerns a tomography apparatus with an annular channel and with at least one ventilation element for drawing off an air current flowing through said annular channel.

2. Description of the Prior Art

Using a tomography apparatus, such as a computed tomography apparatus for example, three-dimensional layered images are created of an area to be examined in a patient for the purposes of diagnosis or therapy. The basic structure of a computed tomography apparatus includes a gantry with a stationary supporting frame in which a rotational frame is mounted such that it can be rotated around an axis. Electronic components of a tomography data acquisition system are disposed on the rotational frame, such that through the rotation of the rotational frame with simultaneous constant forward motion of a patient located on a table along the system axis, projections are recorded from numerous different projection directions at various positions of the area being examined. The projections recorded by means of a spiral shaped sampling of this type are transferred to a computing device and converted to a three-dimensional layered image.

A basic thermal problem for all computed tomography apparatuses is that up to 99% of the electrical energy used in generating X-rays is converted to heat. In order to ensure that the operation of the data acquisition system can ensue without problems, it is necessary to draw away the heat generated by the components disposed on the rotational frame. This can be a particularly large challenge when, for sampling the region being examined, a high level of X-ray radiation is required. In such a case, overheating of the X-ray tube must be avoided. The detector must also be cooled during the operation of the computed tomography apparatus, because with increasing heat the signal/noise ratio of the acquired values becomes worse, which results in a reduction of the image quality of reconstructed layered images.

For this reason, computed tomography apparatuses are equipped with a cooling device for cooling the components located on the rotational frame. In principle, a distinction is made between water cooled systems and air cooled systems. Water cooled systems have the advantage that heat generated within the apparatus can be effectively dissipated without heating the surrounding air. These systems can therefore be operated independently of an existing air conditioning apparatus in the examination room. Water cooled systems, however, are very expensive. A less expensive means for cooling a computed tomography apparatus typically is a cooling device that draws air from the examination room and directs it through the computed tomography apparatus. With this system, the air absorbs a portion of the heat given off by the components. The air current heated in this manner is subsequently channeled out of the space by a ventilation element.

Aside from the actual cooling, the reduction of acoustic emissions caused by the cooling system while operating the computed tomography apparatus is an important aspect in the development of the system. Measures for reducing noise are known is this respect, for example, from DE 10 2005 041 542 A1. Between the rotational frame and the supporting frame, an annular channel is formed. The rotational frame, in the known case, contains openings that are distributed randomly on the rotational frame. When the rotational frame is rotating, these openings pass over the gaps incorporated in the supporting frame in a cyclical manner. In this manner, an exchange of air can be produced by means of a constant fluctuation in pressure, which results in a reduction of acoustic emissions.

SUMMARY OF THE INVENTION

An object of the present invention is to provide a tomography apparatus wherein acoustic emissions during operation of an air cooled tomography apparatus are further reduced.

This object is achieved by a tomography apparatus according to the invention that has at least one ventilation element for the purpose of drawing off an air current flowing through the inside of the tomography apparatus, and the ventilation element has an intake window that is configured to draw off at least a part of the air current from the inside of the tomography apparatus, and, in order to achieve a uniform air flow profile at the output window of the ventilation element, the intake window has a larger effective intake cross-section in its two side regions than in its middle region.

The invention is based on the insight that a significant portion of the acoustic emission that occurs during operation of the tomography apparatus is caused by the high speeds of the current at the direction panels of the output window.

Due to the friction between the air current and the annular channel walls, the air flow through the annular channel, as seen at the cross-section, does not travel in a regular manner at a constant speed. The values of the speed vectors are highest at the middle of the cross-section and decrease toward the edge of the annular channel. The flow profile of the air current in the annular channel thus has a Gaussian form. In this context, flow profile is understood to mean the gradient of the speed vectors within the cross-section.

The invention is based on the recognition that the acoustic emissions in the region of the output window, particularly due to high current speeds to the direction panels, originate from the middle region of the output window. Strong air currents in this area cause, specifically, turbulence and air flow interruptions and thereby fluctuations in pressure, which are perceived as disturbing noises.

In order to reduce the acoustic emissions in identical air flows, or to increase the air flow while maintaining the same acoustic emissions, in accordance with the invention the air current through a special structure of the intake window, is modified so as to even out the flow profile at the output window. In this manner, selectively occurring peaks in the air flow speed are avoided and acoustic emissions are reduced. This is accomplished in that the intake window has a larger effective intake cross section at the sides.

The intake section is a connecting line that, by projection, connects the upper and lower sections of the intake window and runs perpendicular to an annular channel axis defined by a virtual projection plane perpendicular to the intake current.

By means of the larger intake cross-section in the sides, a larger portion of the air flow is drawn off at these areas than in the middle. As a result of the lower speed at which the air flows, by sizing the intake cross-section appropriately the air flow per unit of time transported to the output window can be kept nearly constant throughout the cross-section. In this manner a higher air flow and thereby a greater cooling effect is obtained.

In an embodiment of the invention, the tomography apparatus contains an annular channel through which the air current flows and in which the intake window of the ventilation element is located. An upper section of the intake window corresponding to an outer contour of the annular channel has a convex form. Thereby, the ventilation element can be easily integrated in the housing of the tomography apparatus and in a special case, can form a part of the housing.

The ventilation element furthermore contains a paddle, the front edge of which forms the lower section of the intake window. The ventilation element contains thereby individual structural groups, such that a simple fabrication and installment is possible.

Due to the modular construction of the ventilation element from individual structural groups it is possible to obtain various configurations with different intake cross-sections in a simple manner using the same components.

The front edge of the paddle is normally convex in the direction of the outer annular channel wall, such that at the sides a greater effective intake cross-section is obtained in comparison with the middle. The intake cross-section can furthermore be increased by means of extending the edges of the paddle into the annular channel. The edges extend thereby in the opposite direction of the direction of flow in the annular channel.

A rear edge of the paddle ideally forms a closure with a housing of the ventilation element and is a straight edge. Thereby, the conditions are obtained for a simple rotation of the paddle around a rotational axis running through said edge. By means of the displaceable mounting of the paddle, variously effective intake cross-sections can be established. Different sized intake cross-sections are obtained with the paddle tilted at specific angles to the air flow direction.

The ventilation element functions as a flow separator in that it draws off a specific portion of the air flow in the annular channel. The tomography apparatus contains, in a further embodiment, multiple, for example three, ventilation elements that are arranged sequentially in a row following the flow direction of the air current, whereby the effective intake cross-section of the ventilation elements draws off the air flow by means of the ventilation elements in equal parts. By means of the constantly increasing intake cross-sections, it is ensured that the quantity of air drawn off by the respective ventilation elements remains nearly constant.

For effective deflection of the air flowing out into the vicinity, the tomography apparatus advantageously contains direction panels, which are distributed across the output window. Thereby, a modification of the current direction of the air current flowing from the output window should be affected such that a person standing next to the annular channel of the tomography apparatus is not disturbed by the air flow.

DESCRIPTION OF THE PREFERRED EMBODIMENTS

Figure 1:
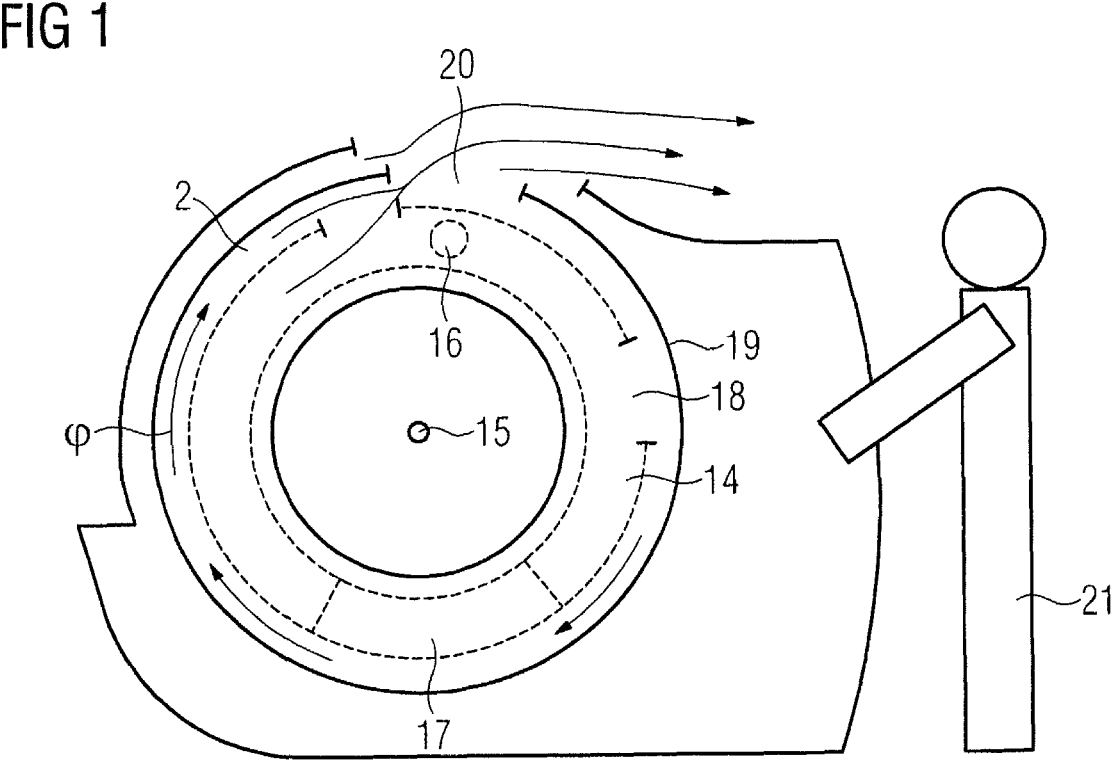
FIG. 1 is a front view of a computer tomography apparatus, wherein the main components of a gantry inside the housing is represented by a broken line.
Figure 2:
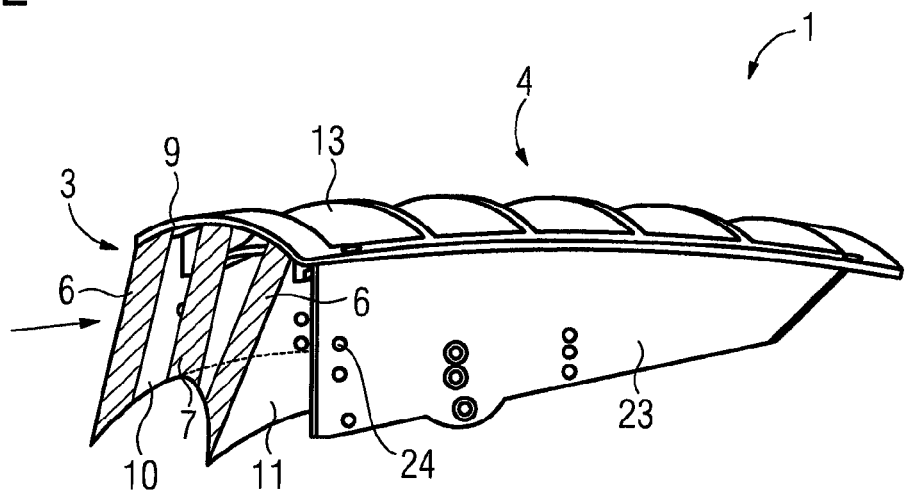
FIG. 2 is a perspective view of a ventilation element of the computer tomography apparatus of the invention in accordance with a design example.
Figure 3:
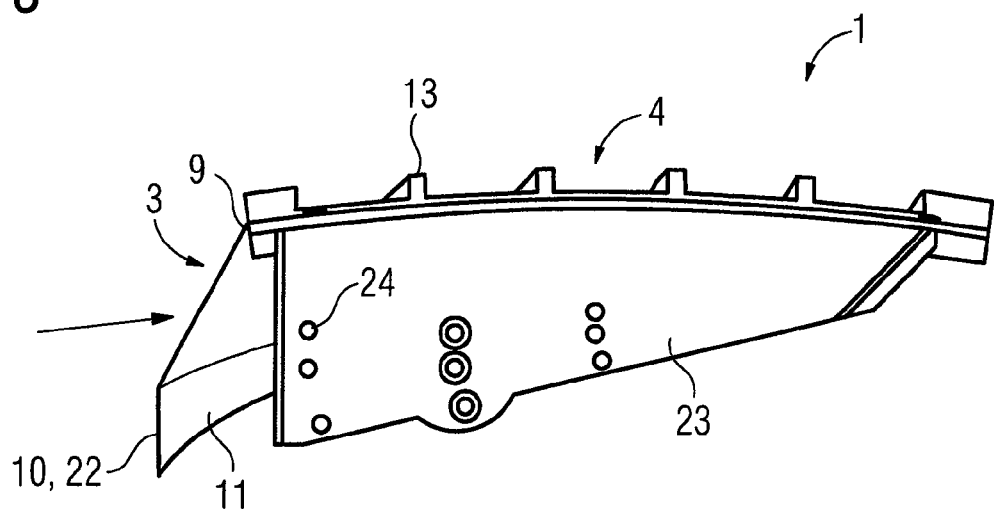
FIG. 3 is a side view of the ventilation element shown in FIG. 2.

FIG. 1 shows a tomography apparatus, in this case a computed tomography apparatus, first without a ventilation element 1 shown in FIG. 2 and FIG. 3. Inside the apparatus there is a rotational frame 14 which can rotate on an axis 15 in the $\phi$-direction shown. For cooling electronic components disposed on the rotational frame 14, such as, for example an X-ray tube 16 and a detector 17, the air is first directed toward the inside of the rotational frame 14. The directing of the air can be accomplished by means of a mount, not shown, with which the rotational frame 14 can also be tilted. In the rotational frame 14, a portion of the heat generated by the components is drawn off and subsequently directed through openings 18 to an annular channel 2 formed between a supporting frame 19 and the rotational frame 14. The annular channel 2 contains a gap 20 above the computer tomography apparatus such that the air current flowing through the annular channel 2 can be redirected through the gap 20 into the surrounding environment.

Without taking further measures, the passage of air over the openings 18 in the area of the gap 20 would lead to a difference in pressure and thereby result in a pulsating emission of the air, which is associated with turbulence and air flow interruptions. Turbulence and air flow interruptions lead to noise emissions and to excessive noise for an operator 21 or a patient.

The air current, furthermore, exits in a tangential direction to the rotational motion $\phi$ of the rotational frame. If the gap 20 is located in the upper region of the computer tomography apparatus, the air may be blown directly in the face of the operator 21 standing next to the gantry, which, in addition to the noise level, is uncomfortable, and would lead to a decrease in operating comfort.

For these reasons, the computer tomography apparatus contains a ventilation element 1 which is shown in FIG. 2 from a perspective view and in FIG. 3 from a side view, and which can be integrated in the gap 20 shown in FIG. 1, and with which a certain portion of the air current can be diverted from the annular channel 2 and released into the surrounding environment.

The ventilation element 1 contains an intake window 3 and an output window 4, by means of which at least a portion of the air current is diverted from the annular channel 2 into the ventilation element 1 and subsequently out of said. The intake window 3 is located in the annular channel 2 for this purpose and covers a part of the cross-section surface of the annular channel 2. The output window 3 in the assembled state is an integral component of the housing of the computer tomography apparatus and has the same convex type structure of the housing. An upper section 9 of the intake window 3 is also convex shaped and borders the housing.

Figure 7:
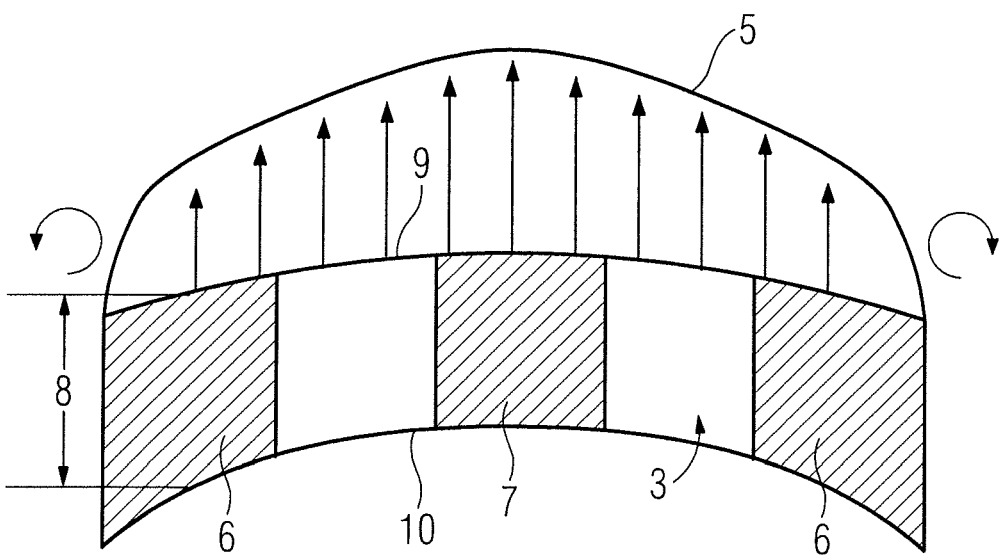
FIG. 7 shows an intake window with a larger effective intake cross-section in the sides with the associated flow profile.

In order to minimize the noise level of the air current at the output window 4 across the width of the ventilation element 1 with a flow profile 5 shown in FIG. 7 which is as even, or respectively, level as possible, the intake window 3 is structured in such a manner that in the sides 6 a larger effective intake cross-section 8 is available than in the middle 7.

This is obtained in the embodiment examples shown by means of, on the one hand, the lower section 10 of the intake window 2 having a convex shape with a curvature which is greater than the curvature of the upper section 9. The vertical distance between the upper section 9 and the lower section 10 of the intake window 3 is thereby greater at the sides 6 than the distance in the middle 7.

Figure 4:
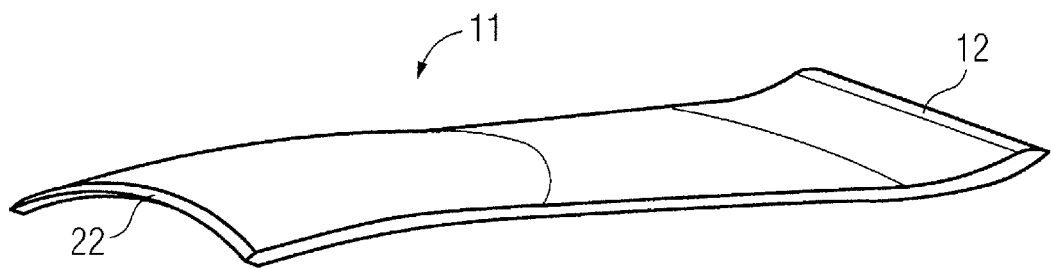
FIG. 4 shows a paddle of the ventilation element in a first design example.

The lower section 10 of the intake window 3 is formed thereby by a front edge 22 of a paddle 11 shown in FIG. 4. The rear edge 12 of the paddle 11 is a straight edge, in order that a closure of the output window 4 may be formed.

The paddle 11 is located between two parallel side walls 23 of a housing frame and arranged in the rear edge 12 in such a manner that it can be rotated such that in various positions different sizes of intake cross-sections in the intake window can be formed as is indicated in FIG. 7 with the reference number 8.

In the simplest case, the paddle ills mounted between the side walls and held in position by means of pins and holes 24, whereby for the reasons of clarity, only one hole is provided with a reference number. By means of an additionally provided screw connection, the paddle 11 can be firmly attached.

Figure 5:
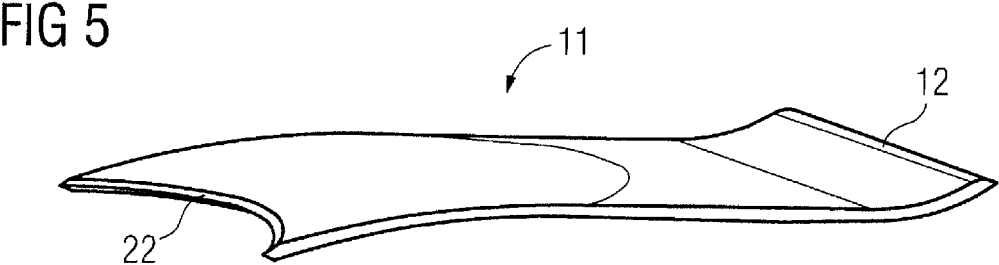
FIG. 5 shows a paddle of the ventilation element in a second design example.

In order to increase the effective intake cross-section 8, the edges of the paddle 11, as is shown in FIG. 5, can be extended such that they extend into the annular channel 2. It is also conceivable that the two shapes of the front edge 22 of the paddle 11 from the FIGS. 4 and 5 can be used in combination for the purpose of increasing the effective intake cross-section.

The output window 4 is comprised of a cover, which is shaped such that it fits the outer circumference of the annular channel 2. The output window 4 contains means for redirection in the form of direction panels 13 for redirecting a current direction of the air, which are distributed across the surface bordered by the opening of the output window 4. For reasons of clarity, only one direction panel with a reference number is provided. The direction panels 13, on the one hand, redirect the escaping air current in one of the directions which can be applied to the direction panel 13. The escaping air current may be directed, for example, directly toward the ceiling of the examination room. In this manner, it no longer is able to blow directly in the face of an operator 21.

The direction panels 13 produce a certain interruption of the direct sound path from the annular channel 2 in the surrounding environment, because the direction panels 13 are distributed across the output opening 4. The direction panels 13 have thereby an optimal current shape and reduce furthermore the effects of pressure fluctuations, such that turbulence and air flow interruption and the thereby associated noise development can be undermined for the most part.

Figure 6:
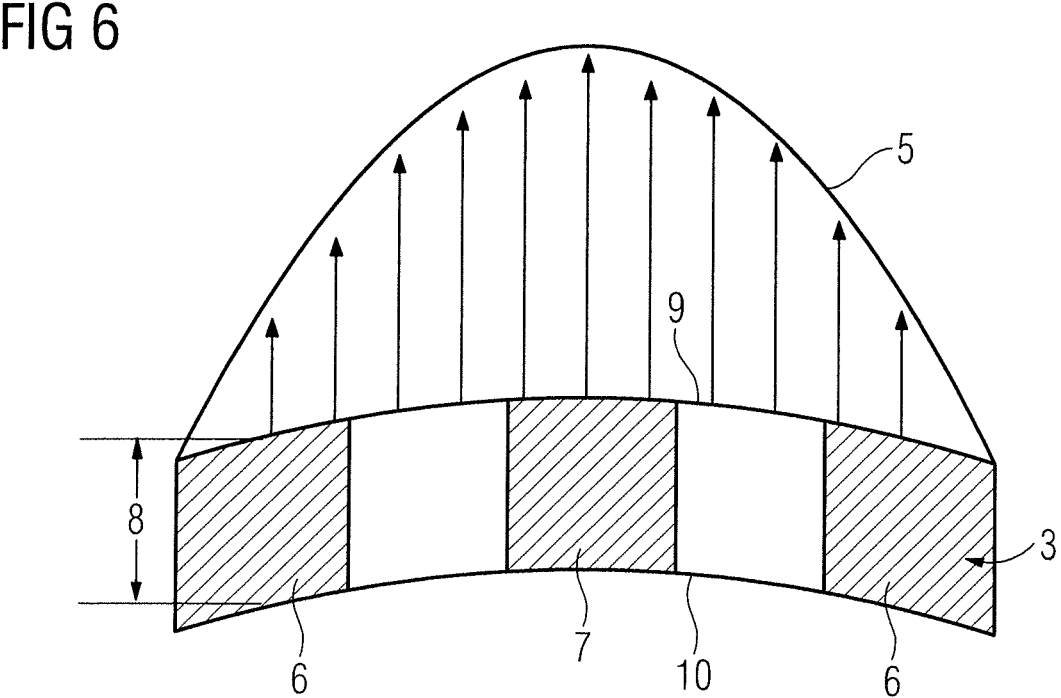
FIG. 6 shows an intake window without a larger effective intake cross-section in the sides with the associated flow profile.

In FIGS. 6 and 7, two intake windows 3 with corresponding flow profiles 5 are shown. In the intake window 3 shown in FIG. 6, the sides 6 do not have a larger effective intake cross-section than those in the middle 7. The flow profile 5 has a Gaussian shape. The large speed vectors in the middle 7 of the intake opening 3 cause strong noise emissions at the direction panels 13 of the output opening 4. In FIG. 7 the effective intake cross-sections 8 in the sides 6, in contrast thereby, to said in the middle 7, are increased. This results in an evening out or leveling of the flow profile 5. By this means, the observed maximal values of the speed vectors are reduced. Although the speed vectors at the edges are larger than those shown in the example in FIG. 6, the reduction of the maximal occurring values of the speed vectors has the effect of strongly reducing noise levels.

In summary, invention relates to a tomography apparatus with an annular channel 2 and with at least one ventilation element 1 for drawing off an air current flowing through the annular channel 2, wherein the ventilation element contains an intake window 3 for the purpose of drawing off at least a portion of the air current. The intake window 3 has a greater effective intake cross-section at the sides 6 than in the middle 7 in order to obtain an even flow profile 5 at the output window 4 of the ventilation element 1. By flattening the flow profile 5 at the output window 4, turbulence and air flow interruptions in the air can effectively be avoided such that when operating the tomography apparatus, disturbing acoustic emissions can be reduced, or a higher air flow rate, and thus a greater cooling effect, can be obtained.

Although modifications and changes may be suggested by those skilled in the art, it is the intention of the inventor to embody within the patent warranted hereon all changes and modifications as reasonably and properly come within the scope of his contribution to the art.

We claim as our invention:

1. A tomography apparatus comprising:
   an apparatus frame having an interior containing heat-generating components;
   a flow-generating arrangement in said interior of said apparatus frame that generates a flow of air within said interior of said apparatus frame to convey heat away from said heat-generating components;
   a ventilation element mounted at said apparatus frame and having a passage therein that communicates the interior of said apparatus frame with an exterior of said apparatus frame to allow air flow through said ventilation element between an intake window of said ventilation element, located in said interior of said apparatus frame, and a discharge opening of said ventilation element located at said exterior of said apparatus frame; and
   said intake window comprising a middle region and respective side regions on opposite sides of said middle region, said side regions having an effective air intake cross-section that is larger than an effective air intake cross-section of said middle region in order to produce a substantially uniform flow profile of air at said discharge window of said ventilation element.

2. A tomography apparatus as claimed in claim 1 wherein that said apparatus frame comprises an annular channel therein in which said air flows, and in which said intake window is located.

3. A tomography apparatus as claimed in claim 2 wherein said intake window comprises an upper section having a convex shape conforming to an outer contour of said annular channel.

4. A tomography apparatus as claimed in claim 1 wherein said ventilation element comprises a paddle having a front edge forming a roller section of said intake window.

5. A tomography apparatus as claimed in claim 4 wherein said ventilation element comprises a housing, and wherein said paddle comprises a straight rear edge forming a closure with said housing.

6. A tomography apparatus as claimed in claim 5 wherein said paddle is mounted for rotation around an axis proceeding through said straight edge allowing adjustment of said paddle to produce different effective air intake cross-sections of said intake window.

7. A tomography apparatus as claimed in claim 1 wherein said flow generating arrangement generates said flow of air in said interior of said annular frame in a flow direction, and wherein said ventilation element is a first ventilation element, said tomography apparatus comprising a plurality of additional ventilation elements corresponding to said first ventilation element located at said apparatus frame at successive locations along said direction of said flow of air, said traditional ventilation elements respectively having successively larger intake cross-sections along said direction of said flow of air.

8. A tomography apparatus as claimed in claim 1 wherein said ventilation element comprises direction panels distributed across said discharge window that modify a direction of flow of said air from said discharge window.

* * * * *